(12) United States Patent
Xue et al.

(10) Patent No.: US 11,939,599 B2
(45) Date of Patent: Mar. 26, 2024

(54) GENE MINING METHOD COMBINING FUNCTIONAL SEQUENCE AND STRUCTURE SIMULATION, NADH-PREFERRING PHOSPHINOTHRICIN DEHYDROGENASE MUTANT AND APPLICATION THEREOF

(71) Applicant: ZHEJIANG UNIVERSITY OF TECHNOLOGY, Hangzhou (CN)

(72) Inventors: Yaping Xue, Hangzhou (CN); Feng Cheng, Hangzhou (CN); Jiamin Zhang, Hangzhou (CN); Shuping Zou, Hangzhou (CN); Jianmiao Xu, Hangzhou (CN); Yuguo Zheng, Hangzhou (CN)

(73) Assignee: ZHEJIANG UNIVERSITY OF TECHNOLOGY, Hangzhou (CN)

( * ) Notice: Subject to any disclaimer, the term of this patent is extended or adjusted under 35 U.S.C. 154(b) by 0 days.

(21) Appl. No.: 17/566,373

(22) Filed: Dec. 30, 2021

(65) Prior Publication Data
US 2022/0204949 A1 Jun. 30, 2022

(51) Int. Cl.
*C12N 9/00* (2006.01)
*C12N 9/04* (2006.01)
*C12N 9/06* (2006.01)
*C12P 13/04* (2006.01)
*G16B 30/10* (2019.01)

(52) U.S. Cl.
CPC ......... *C12N 9/0016* (2013.01); *C12N 9/0006* (2013.01); *C12P 13/04* (2013.01); *G16B 30/10* (2019.02); *C12Y 104/01002* (2013.01); *C12Y 104/01003* (2013.01); *C12Y 104/01004* (2013.01)

(58) Field of Classification Search
CPC ..... C12N 9/0016; C12N 9/0006; C12P 13/04; C12Y 104/01002; C12Y 104/01003; C12Y 104/01004; C12Y 101/01047

USPC ....................................................... 435/320.1
See application file for complete search history.

(56) References Cited

U.S. PATENT DOCUMENTS
6,936,444 B1  8/2005  Bartsch

OTHER PUBLICATIONS

CAO Cheng-Hao et al., Efficient synthesis of L-phosphinothricin using a novel aminoacylase mined from Stenotrophomonas maltophilia. Enzyme and Microbial Technology, 135 (2020) 109493.

*Primary Examiner* — Robert B Mondesi
*Assistant Examiner* — Mohammad Y Meah
(74) *Attorney, Agent, or Firm* — Jiwen Chen; Joywin IP Law PLLC

(57) ABSTRACT

Disclosed are a gene mining method combining functional sequence and structure simulation, an NADH-preferring phosphinothricin dehydrogenase mutant and an application thereof. The gene mining method comprises the following steps: (1) analyzing a characteristic sequence which an NADH-type glutamate dehydrogenase should have; (2) searching a gene library based on the characteristic sequence; (3) performing clustering analysis and protein structure simulation on genes obtained by the searching; (4) selecting genes that feature high gene aggregation and a protein structure similar to that of the known phosphinothricin dehydrogenase as candidate genes. A wild-type phosphinothricin dehydrogenase with an amino acid sequence as set forth in SEQ ID No.2 derived from Lysinibacillus composti is obtained through the gene mining, and then mutated, and an NADH-preferring phosphinothricin dehydrogenase mutant is screened out, which has a mutation site selected from one of the following: (1) A144G-V375F-M91A; (2) A144G-V345A-M91A; (3) A144G. This mutant enzyme can be used for catalytic reaction with an inexpensive coenzyme NAD.

6 Claims, 3 Drawing Sheets
Specification includes a Sequence Listing.

SEQUENCE LISTING

```
<160> NUMBER OF SEQ ID NOS: 24

<210> SEQ ID NO 1
<211> LENGTH: 1242
<212> TYPE: DNA
<213> ORGANISM: Artificial Sequence
<220> FEATURE:
<223> OTHER INFORMATION: Synthesized

<400> SEQUENCE: 1
atggcagaaa acctgaactt atttacgagc acccaggagg ttgtgaaaga agcgctgaac      60
aaactgggtt atgatgaggc aatgtacgaa ctgctgaaag aaccgctgcg cctgctgaaa     120
gtgcgtattc ctgtgaagat ggacgatggc accacacagg tgtttacggg ttatcgcgca     180
caacattccg atgcagtagg tcccaccaaa ggtgcgtgc gttttcatcc tatggtttct     240
gaagacgaag ttaaagcact gagcatgtgg atgaccctga agtgcgggat tgtagatctg     300
ccttatggtg gtgtaaagg tggcattatt tgtgatccgc gtcagatgag catggggaa      360 ttagaacgtc tgagccgtgg atatgttcgg gcaattagtc agattgttgg gccgaccaaa     420
gatataccgg caccggatgt ttttaccaat gcacaaatta tggcatggat gatggatgag     480
tatagccgta tggatgaatt taatagtccg ggttttataa ccggtaaacc tctggtgctg     540
ggcggtagta aagggcgtga tcgggcgacg gcagaaggtg ttacgattgt tattcaggag     600
gcagcaaaaa agagaaatat cgatatcaaa ggtgcacgcg ttgttattca agggttcggt     660
aatgccggca gttttttagc aaagtttatg agtgatctgg gcgcgaaggt tataggaata     720
agtgatgcat acggggccct gcacgatccg aatggtttag atattgatta tctgctggac     780
agacgtgata gttttggtac cgttaccacg ctgtttgaaa ataatcaattac gaatcaggag     840 ctgctggaac tggattgtga tattctggtg ccggccgcaa ttgagaatca gattacggca     900
```

-continued

```
gaaaatgcac ataatattaa ggcaaccata gttgtggaag cagcgaacgg cccaaccacc        960
tctgaagcaa ccaaaattct gaccgaacgt ggtattctgt tagtgccaga cgttttagca       1020
agcgcaggtg gggttacagt tagctacttt gagtgggttc aaaataatat gggctattac       1080
tgggaagaag aagaggttca agaaaaactg tacaaaaaaa tggtggatag ctttgaagca       1140
gtatatacaa ccgcaaccac gcgcaatata gatatgcgtc tggcagcgta tatggtggga       1200
gtgagaagaa cagcagaagc gagccgtttc cggggctggg tg                         1242
```

<210> SEQ ID NO 2
<211> LENGTH: 414
<212> TYPE: PRT
<213> ORGANISM: Lysinibacillus composti

<400> SEQUENCE: 2

```
Met Ala Glu Asn Leu Asn Leu Phe Thr Ser Thr Gln Glu Val Val Lys
1               5                  10                  15

Glu Ala Leu Asn Lys Leu Gly Tyr Asp Glu Ala Met Tyr Glu Leu Leu
                20                  25                  30

Lys Glu Pro Leu Arg Leu Leu Lys Val Arg Ile Pro Val Lys Met Asp
            35                  40                  45

Asp Gly Thr Thr Gln Val Phe Thr Gly Tyr Arg Ala Gln His Ser Asp
        50                  55                  60

Ala Val Gly Pro Thr Lys Gly Val Arg Phe His Pro Met Val Ser
65                  70                  75                  80

Glu Asp Glu Val Lys Ala Leu Ser Met Trp Met Thr Leu Lys Cys Gly
                85                  90                  95

Ile Val Asp Leu Pro Tyr Gly Gly Lys Gly Ile Ile Cys Asp
                100                 105                 110

Pro Arg Gln Met Ser Met Gly Glu Leu Glu Arg Leu Ser Arg Gly Tyr
            115                 120                 125

Val Arg Ala Ile Ser Gln Ile Val Gly Pro Thr Lys Asp Ile Pro Ala
        130                 135                 140

Pro Asp Val Phe Thr Asn Ala Gln Ile Met Ala Trp Met Met Asp Glu
145                 150                 155                 160

Tyr Ser Arg Met Asp Glu Phe Asn Ser Pro Gly Phe Ile Thr Gly Lys
                165                 170                 175

Pro Leu Val Leu Gly Gly Ser Lys Gly Arg Asp Arg Ala Thr Ala Glu
            180                 185                 190

Gly Val Thr Ile Val Ile Gln Glu Ala Ala Lys Lys Arg Asn Ile Asp
        195                 200                 205

Ile Lys Gly Ala Arg Val Val Ile Gln Gly Phe Gly Asn Ala Gly Ser
    210                 215                 220

Phe Leu Ala Lys Phe Met Ser Asp Leu Gly Ala Lys Val Ile Gly Ile
225                 230                 235                 240

Ser Asp Ala Tyr Gly Ala Leu His Asp Pro Asn Gly Leu Asp Ile Asp
                245                 250                 255

Tyr Leu Leu Asp Arg Arg Asp Ser Phe Gly Thr Val Thr Thr Leu Phe
            260                 265                 270

Glu Asn Thr Ile Thr Asn Gln Glu Leu Leu Leu Asp Cys Asp Ile
        275                 280                 285

Leu Val Pro Ala Ala Ile Glu Asn Gln Ile Thr Ala Glu Asn Ala His
    290                 295                 300

Asn Ile Lys Ala Thr Ile Val Val Glu Ala Ala Asn Gly Pro Thr Thr
305                 310                 315                 320
```

Ser Glu Ala Thr Lys Ile Leu Thr Glu Arg Gly Ile Leu Val Pro
            325                 330                 335

Asp Val Leu Ala Ser Ala Gly Gly Val Thr Val Ser Tyr Phe Glu Trp
        340                 345                 350

Val Gln Asn Asn Met Gly Tyr Tyr Trp Glu Glu Glu Val Gln Glu
    355                 360                 365

Lys Leu Tyr Lys Lys Met Val Asp Ser Phe Glu Ala Val Tyr Thr Thr
    370                 375                 380

Ala Thr Thr Arg Asn Ile Asp Met Arg Leu Ala Ala Tyr Met Val Gly
385                 390                 395                 400

Val Arg Arg Thr Ala Glu Ala Ser Arg Phe Arg Gly Trp Val
            405                 410

<210> SEQ ID NO 3
<211> LENGTH: 6
<212> TYPE: PRT
<213> ORGANISM: Artificial Sequence
<220> FEATURE:
<223> OTHER INFORMATION: Synthesized

<400> SEQUENCE: 3

Gly Gly Gly Lys Gly Gly
1               5

<210> SEQ ID NO 4
<211> LENGTH: 4
<212> TYPE: PRT
<213> ORGANISM: Artificial Sequence
<220> FEATURE:
<223> OTHER INFORMATION: Synthesized

<400> SEQUENCE: 4

Val Val Thr Gly
1

<210> SEQ ID NO 5
<211> LENGTH: 4
<212> TYPE: PRT
<213> ORGANISM: Artificial Sequence
<220> FEATURE:
<223> OTHER INFORMATION: Synthesized

<400> SEQUENCE: 5

Phe Val Thr Gly
1

<210> SEQ ID NO 6
<211> LENGTH: 4
<212> TYPE: PRT
<213> ORGANISM: Artificial Sequence
<220> FEATURE:
<223> OTHER INFORMATION: Synthesized

<400> SEQUENCE: 6

Val Leu Thr Gly
1

<210> SEQ ID NO 7
<211> LENGTH: 4
<212> TYPE: PRT
<213> ORGANISM: Artificial Sequence
<220> FEATURE:
<223> OTHER INFORMATION: Synthesized

```
<400> SEQUENCE: 7

Val Phe Thr Gly
1

<210> SEQ ID NO 8
<211> LENGTH: 4
<212> TYPE: PRT
<213> ORGANISM: Artificial Sequence
<220> FEATURE:
<223> OTHER INFORMATION: Synthesized

<400> SEQUENCE: 8

Phe Ile Thr Gly
1

<210> SEQ ID NO 9
<211> LENGTH: 4
<212> TYPE: PRT
<213> ORGANISM: Artificial Sequence
<220> FEATURE:
<223> OTHER INFORMATION: Synthesized

<400> SEQUENCE: 9

Phe Phe Thr Gly
1

<210> SEQ ID NO 10
<211> LENGTH: 4
<212> TYPE: PRT
<213> ORGANISM: Artificial Sequence
<220> FEATURE:
<223> OTHER INFORMATION: Synthesized

<400> SEQUENCE: 10

Val Val Phe Gly
1

<210> SEQ ID NO 11
<211> LENGTH: 5
<212> TYPE: PRT
<213> ORGANISM: Artificial Sequence
<220> FEATURE:
<223> OTHER INFORMATION: Synthesized

<400> SEQUENCE: 11

Phe Val Phe Thr Gly
1               5

<210> SEQ ID NO 12
<211> LENGTH: 4
<212> TYPE: PRT
<213> ORGANISM: Artificial Sequence
<220> FEATURE:
<223> OTHER INFORMATION: Synthesized

<400> SEQUENCE: 12

Val Leu Phe Gly
1

<210> SEQ ID NO 13
<211> LENGTH: 4
<212> TYPE: PRT
<213> ORGANISM: Artificial Sequence
<220> FEATURE:
<223> OTHER INFORMATION: Synthesized

<400> SEQUENCE: 13
```

Val Phe Phe Gly
1

<210> SEQ ID NO 14
<211> LENGTH: 4
<212> TYPE: PRT
<213> ORGANISM: Artificial Sequence
<220> FEATURE:
<223> OTHER INFORMATION: Synthesized

<400> SEQUENCE: 14

Phe Leu Phe Gly
1

<210> SEQ ID NO 15
<211> LENGTH: 4
<212> TYPE: PRT
<213> ORGANISM: Artificial Sequence
<220> FEATURE:
<223> OTHER INFORMATION: Synthesized

<400> SEQUENCE: 15

Phe Phe Phe Gly
1

<210> SEQ ID NO 16
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (2)..(2)
<223> OTHER INFORMATION: Xaa is any kind of amino acid residue
<220> FEATURE:
<221> NAME/KEY: misc_feature
<222> LOCATION: (5)..(6)
<223> OTHER INFORMATION: Xaa is any kind of amino acid residue

<400> SEQUENCE: 16

Gly Xaa Arg Val Xaa Xaa Gly
1               5

<210> SEQ ID NO 17
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (5)..(6)
<223> OTHER INFORMATION: n is a, c, g or t
<220> FEATURE:
<221> NAME/KEY: misc_feature
<222> LOCATION: (7)..(7)
<223> OTHER INFORMATION: k is g or t

<400> SEQUENCE: 17
accgnnkccg gatgtttttta ccaatgc                                          27

<210> SEQ ID NO 18
<211> LENGTH: 27
<212> TYPE: DNA
<213> ORGANISM: Artificial Sequence
<220> FEATURE:
<223> OTHER INFORMATION: Synthesized
<220> FEATURE:

```
<221> NAME/KEY: misc_feature
<222> LOCATION: (6)..(6)
<223> OTHER INFORMATION: m is a or c
<220> FEATURE:
<221> NAME/KEY: misc_feature
<222> LOCATION: (7)..(8)
<223> OTHER INFORMATION: n is a, c, g or t

<400> SEQUENCE: 18
tccggmnncg gtatatcttt ggtcggc                                              27

<210> SEQ ID NO 19
<211> LENGTH: 28
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (5)..(6)
<223> OTHER INFORMATION: n is a, c, g or t
<220> FEATURE:
<221> NAME/KEY: misc_feature
<222> LOCATION: (7)..(7)
<223> OTHER INFORMATION: k is g or t

<400> SEQUENCE: 19
tgggnnkaca gttagctact ttgagtgg                                             28

<210> SEQ ID NO 20
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (7)..(7)
<223> OTHER INFORMATION: m is a or c
<220> FEATURE:
<221> NAME/KEY: misc_feature
<222> LOCATION: (8)..(9)
<223> OTHER INFORMATION: n is a, c, g or t

<400> SEQUENCE: 20
aactgtmnnc ccacctgcgc ttgctaa                                              27

<210> SEQ ID NO 21
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (7)..(8)
<223> OTHER INFORMATION: n is a, c, g or t
<220> FEATURE:
<221> NAME/KEY: misc_feature
<222> LOCATION: (9)..(9)
<223> OTHER INFORMATION: k is g or t

<400> SEQUENCE: 21
aaaatgnnkg atagctttga agcagtata                                            29

<210> SEQ ID NO 22
<211> LENGTH: 30
<212> TYPE: DNA
<213> ORGANISM: Artificial Sequence
<220> FEATURE:
<223> OTHER INFORMATION: Synthesized
```

```
<220> FEATURE:
<221> NAME/KEY: misc_feature
<222> LOCATION: (7)..(7)
<223> OTHER INFORMATION: m is a or c
<220> FEATURE:
<221> NAME/KEY: misc_feature
<222> LOCATION: (8)..(9)
<223> OTHER INFORMATION: n is a, c, g or t

<400> SEQUENCE: 22
gctatcmnnc atttttttgt acagttttc                                      30

<210> SEQ ID NO 23
<211> LENGTH: 28
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (8)..(9)
<223> OTHER INFORMATION: n is a, c, g or t
<220> FEATURE:
<221> NAME/KEY: misc_feature
<222> LOCATION: (10)..(10)
<223> OTHER INFORMATION: k is g or t

<400> SEQUENCE: 23
catgtggnnk accctgaagt gcgggatt                                       28

<210> SEQ ID NO 24
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (7)..(7)
<223> OTHER INFORMATION: m is a or c
<220> FEATURE:
<221> NAME/KEY: misc_feature
<222> LOCATION: (8)..(9)
<223> OTHER INFORMATION: n is a, c, g or t

<400> SEQUENCE: 24
cagggtmnnc cacatgctca gtgctttaa                                      29
```

US 11,939,599 B2

GENE MINING METHOD COMBINING FUNCTIONAL SEQUENCE AND STRUCTURE SIMULATION, NADH-PREFERRING PHOSPHINOTHRICIN DEHYDROGENASE MUTANT AND APPLICATION THEREOF

This application claims priority to Chinese Patent Application No. 202011644056.2 filed Dec. 31, 2020, which is hereby incorporated by reference.

Technical Field

The present invention relates to the field of biological technology, in particular to a gene mining method combining functional sequence and structural simulation, an NADH-preferring phosphinothricin dehydrogenase mutant and application thereof.

Background Technology

Phosphinothricin (also known as glufosinate, PPT for short), with a chemical name of 2-amino-4-[hydroxy (methyl)phosphono]-butyric acid, is the second largest herbicide tolerated by transgenic crops in the world. It was first developed and produced by Hoechst (which is now owned by Bayer after several mergers and acquisitions). Phosphinothricin is also known as phosphinothricin ammonium salt, Basta and Buster. Phosphinothricin belongs to phosphonic acid herbicides and non-selective contact herbicides and is a glutamine synthetase inhibitor.

Phosphinothricin has two optical isomers, L-phosphinothricin and D-phosphinothricin. However, only the L-form has physiological activity, and is easily decomposed in the soil, less toxic to humans and animals, wide in herbicidal spectrum and less destructive to the environment.

Phosphinothricin currently available on the market is generally a racemic mixture. If the phosphinothricin product can be used as a pure optical isomer in the L-configuration, the consumption of phosphinothricin can be remarkably reduced, which is of great significance for improving atomic economy, reducing use cost and lowering environmental pressure.

There are three main methods for preparing chiral pure L-phosphinothricin: chiral resolution, chemical synthesis and biocatalysis. The biocatalysis method for producing phosphinothricin has the advantages of strict stereoselectivity, mild reaction conditions, and high yield, and is an advantageous method for producing L-phosphinothricin, which mainly includes the following three categories:

1) L-phosphinothricin is obtained by direct hydrolysis of L-phosphinothricin derivatives as the substrate through an enzyme method. For this route, the main advantages are that the conversion rate is high, and the e.e. value of the product is high, but expensive and difficult-to-obtain chiral raw materials are needed as precursors, resulting in increased cost, which is not conductive to industrialized production. For example, the simplest process for preparing L-phosphinothricin by the biological method is to directly hydrolyze bialaphos by using protease. Bialaphos is a natural tripeptide compound, which, under the catalysis of protease, can lose two molecules of L-alanine to obtain L-phosphinothricin.

2) L-phosphinothricin is obtained through selective resolution of a precursor of racemic phosphinothricin by an enzyme. The main advantages are that the raw materials are relatively easily available, and the catalyst activity is high, but the theoretical yield can only reach 50%, resulting in the waste of raw materials. For example, Cao et al. (Cao C-H, Cheng F, Xue Y-P, Zheng Y-G (2020) Efficient synthesis of L-phosphinothricin using a novel aminoacylase mined from Stenotrophomonas maltophilia. Enzyme and Microbial Technology 135 doi:10.1016/j.enzmictec.2019.109493) performed chiral resolution of N-acetyl-PPT using a novel aminoacylase derived from Stenotrophomonas maltophilia to obtain L-phosphinothricin. Whole cells were used for catalysis, the conversion was >49% in 4 hours and optically pure L-PPT (>99.9% e.e.) was obtained.

3) With α-keto acid-2-carbonyl-4-(hydroxymethylphosphono)butyric acid (PPO) as the substrate, L-phosphinothricin is obtained by asymmetric synthesis with enzymes, mainly including transaminase and phosphinothricin dehydrogenase. Bartsch et al. (Bartsch K (2005) Process for the preparation of 1-phosphinothrcine by enzymatic transamination with aspartate. US Patent no. US6936444B1) used PPO as the substrate, L-aspartic acid as the amino donor to react as catalyzed by transaminase screened and separated from soil microorganisms and having specific enzymatic activity for PPO and L-aspartic acid. With a substrate concentration of 552 mM, the reaction was carried out at a very high temperature (80° C.) for 4 hours, the conversion rate reached 52%, and the space-time yield was 4.5 g L-PPT/g·L$^{-1}$·d$^{-1}$. However, preparation of L-phosphinothricin using transaminase has two major defects. One is that this is a reversible reaction, the raw material PPO cannot be completely converted into L-PPT, and it is impossible for the conversion rate to reach 100%; second, to make the reversible reaction proceed in the direction of producing L-PPT, at least 2 times of L-aspartic acid as the amino donor is needed, whereas excessive aspartic acid brings great trouble to the separation of L-PPT.

Among various enzymatic synthesis routes of phosphinothricin, the ketocarbonyl group in the keto acid intermediate is a latent chiral functional group, with which a chiral center can be constructed through an enzymatic synthesis route; and the keto acid route becomes a route suitable for industrial development and production of L-phosphinothricin because the raw materials are cheap and readily available, and the use of highly toxic cyanides can be avoided.

Amino acid dehydrogenase (EC 1.4.1.X, AADH) is a kind of amino acid dehydrogenase that can achieve reversible deamination of amino acids to produce the corresponding keto acids, which requires the participation of nucleoside coenzyme (NAD$^+$) in the reaction. It has been widely used in the synthesis of natural and non-natural α-amino acids. According to their substrate specificity, amino acid dehydrogenases can be divided into glutamate dehydrogenase, leucine dehydrogenase, alanine dehydrogenase, and valine dehydrogenase or the like. An amino acid dehydrogenase will be called "phosphinothricin dehydrogenase (PPTDH)" if it shows activity towards phosphinothricin precursors.

Glucose dehydrogenase (EC1.1.1.47, GDH) is an important biocatalytic coenzyme for the regeneration and circulation of coenzyme NADH in the redox catalytic reaction.

Although the enzymatic activity of NADPH-preferring phosphinothricin dehydrogenase is slightly higher than that of NADH-preferring phosphinothricin dehydrogenase (more than 50 times), the market price of NADPH (about 20,000 yuan per ton) is five times that of NADH. In practical application, the addition of exogenous NADPH will lead to a significant increase in the cost of the product L-phosphinothricin. Therefore, an NADH-preferring high-activity phosphinothricin dehydrogenase is invented, which, in conjunction with exogenous low-cost NADH or NAD, has a good application prospect.

SUMMARY OF THE INVENTION

In view of the problem that the asymmetric reductive amination activity of the existing phosphinothricin dehydrogenase on 2-carbonyl-4-(hydroxymethylphosphono)-butyric acid is not high, an object of the present invention is to provide an NADH-preferring phosphinothricin dehydrogenase mutant, and a recombinant strain constructed using the gene of the NADH-preferring phosphinothricin dehydrogenase mutant and a crude enzyme liquid thereof as a biocatalyst for chiral biosynthesis of L-phosphinothricin.

Disclosed is an NADH-preferring phosphinothricin dehydrogenase mutant which is obtained by mutating a wild-type phosphinothricin dehydrogenase derived from *Lysinibacillus composti*, wherein the wild-type phosphinothricin dehydrogenase has an amino acid sequence as set forth in SEQ ID No.2, and the NADH-preferring phosphinothricin dehydrogenase mutant has a mutation site selected from one of the following:
(1) A144G-V375F-M91A;
(2) A144G-V345A-M91A;
(3) A144G.

Also disclosed is a gene encoding the NADH-preferring phosphinothricin dehydrogenase mutant.

Also disclosed is a recombinant bacterium, which comprises a host cell and a target gene transferred into the host cell, wherein the target gene comprises the aforementioned gene.

Preferably, for the recombinant bacterium, the target gene further comprises a gene encoding glucose dehydrogenase. This allows for co-expression of the phosphinothricin dehydrogenase mutant and glucose dehydrogenase. More preferably, the gene encoding glucose dehydrogenase has a sequence with a GenBank accession number of KM817194.1.

Also disclosed is an application of the NADH-preferring phosphinothricin dehydrogenase mutant, the gene or the recombinant bacterium in preparing L-phosphinothricin.

Also disclosed is a method for preparing L-phosphinothricin, wherein 2-carbonyl-4-(hydroxymethylphosphono)-butyric acid as a substrate is allowed to react as catalyzed by a catalyst in the presence of an inorganic amino donor, a coenzyme regeneration and circulation system and a corresponding co-substrate to obtain L-phosphinothricin; The catalyst is one of the following:
(1) the NADH-preferring phosphinothricin dehydrogenase mutant;
(2) a recombinant bacterium capable of expressing the NADH-preferring phosphinothricin dehydrogenase mutant or a crude enzyme liquid obtained by lysis of the recombinant bacterium.

Preferably, the coenzyme regeneration and circulation system use a coenzyme regeneration and circulation system preferring glucose dehydrogenase, formate dehydrogenase, or alcohol dehydrogenase.

Also provided is a gene mining method combining functional sequence and structural simulation, which comprises the following steps:
(1) analyzing a characteristic sequence of an NADH-type glutamate dehydrogenase, the characteristic sequence includes:
(1.1) protein size: a candidate protein is 300-500 amino acids in length,
(1.2) two necessary characteristic sequences of phosphinothricin dehydrogenase: the first one is GGGKGG, and the second one is one of VVTG, FVTG, VLTG, VFTG, FITG, FFTG, VVFG, FVFG, VLFG, VFFG, FLFG and FFFG;
(1.3) a characteristic sequence binding to NADH: GXRVXXG, wherein X represents any amino acid;
(2) searching a gene library based on the characteristic sequences;
(3) performing clustering analysis and protein structure simulation on the genes obtained in the step (2);
(4) selecting genes featuring high gene aggregation and a protein structure similar to that of the known phosphinothricin dehydrogenase as candidate genes.

When searching the gene library in the step (2), iterative PSI-BLAST search and clustering analysis are performed on the NCBI microbial genome resource and then the NCBI NR sequence database (containing about 100 million protein genes) by using the above characteristic sequences to obtain 15 clusters, wherein the aggregation degrees of the 15 clusters are 0.82, 0.76, 0.71, 0.66, 0.65, 0.58, 0.43, 0.42, 0.40, 0.39, 0.38, 0.34, 0.33, 0.32 and 0.30 respectively (in descending order).

In the step (3), 36 representative proteins (six proteins per cluster) in the six clusters with the highest aggregation degrees are selected to carry out three-dimensional structure simulation (a tencent tFold protein structure server can be adopted), and the simulated structure is structurally compared with known phosphinothricin dehydrogenases (PDB database Nos.: 1LEH, 1BW9 and 5IJZ), wherein the structural standard deviations (RMSD) of LcGDH derived from *Lysinibacillus composti* relative to the three known phosphinothricin dehydrogenases are all less than 2 Å, so the LcGDH gene is selected as the starting gene (as set forth in amino acid sequence SEQ ID No.2).

Compared with the prior art, the present invention has the following beneficial effects:
(1) The phosphinothricin dehydrogenase mutant of the present invention has better catalytic efficiency, and with 2-carbonyl-4-(hydroxymethylphosphono)-butyric acid as a substrate for catalytic reaction, the conversion rate is much higher than that of the wild-type enzyme, and the PPO yield is also greatly improved.
(2) The present invention utilizes the phosphinothricin dehydrogenase mutant and the coenzyme circulation system to catalytically reduce 2-carbonyl-4-[hydroxy(methyl)phosphono]butyric acid into L-phosphinothricin so as to realize asymmetric synthesis of L-phosphinothricin.
(3) According to the present invention, 2-carbonyl-4-[hydroxy(methyl)phosphono]butyric acid can be directly used as a substrate for asymmetric synthesis, expensive chemical resolution reagents are not needed, synthesis of phosphinothricin derivatives is omitted, and cheap coenzyme NAD is used for catalytic reaction. Therefore, compared with the prior production process using coenzyme NADP, the present invention features a obviously reduced cost and a promising prospect in industrial application.

DETAILED DESCRIPTION OF THE EMBODIMENTS

Example 1

Step 1: Analyzing a characteristic sequence that an NADH-type glutamate dehydrogenase should have: (1) protein size: the length of the candidate protein (300-500 amino acids); (2) two necessary characteristic sequences of phosphinothricin dehydrogenase: the first one is GGGKGG, and the second one is one of VVTG, FVTG, VLTG, VFTG, FITG, FFTG, VVFG, FVFTG, VLFG, VFFG, FLFG, and FFFG; (2) a characteristic sequence binding to NADH: GXRVXXG, wherein X represents one of 20 amino acid residues.

Step 2: Searching a gene library: Using the above characteristic sequences, iterative PSI-BLAST search and clustering analysis were performed on the NCBI microbial genomic resource and then the NCBI NR sequence database (containing about 100 million protein genes), and 15 clusters were obtained, wherein the aggregation degrees of the 15 clusters were 0.82, 0.76, 0.71, 0.66, 0.65, 0.58, 0.43, 0.42, 0.40, 0.39, 0.38, 0.34, 0.33, 0.32 and 0.30 respectively (in descending order).

Step 3: 36 representative proteins (six proteins per cluster) in the six clusters with the highest aggregation degrees were selected to carry out three-dimensional structure simulation (using a tencent tFold protein structure server), and the simulated structure was structurally compared with known phosphinothricin dehydrogenases (1LEH, 1BW9 and SIJZ), wherein the structural standard deviations (RMSD) of the LcGDH derived from *Lysinibacillus composti* relative to the three known phosphinothricin dehydrogenases were all less than 2 Å, so the LcGDH gene was selected as the starting gene (as set forth in amino acid sequence SEQ ID No.2).

Example 2: Construction and screening of phosphinothricin dehydrogenase mutant library The amino acid sequence of LcGDH of Example 1 was subjected to codon optimization (the nucleotide sequence obtained after codon optimization is as set forth in SEQ ID No.1), and the LcGDH gene obtained by gene synthesis from Hangzhou Tsingke Biotechnology Co., Ltd. was cloned onto NcoI of MCS1 (multiple cloning site 1) of plasmid pEDuET to construct a recombinant expression vector pET-Duet-LcGDH, with the His-Tag gene of the plasmid being retained. The vector was transferred into E. coli BL21(DE3), which was sent to Hangzhou Tsingke Biotechnology Co., Ltd. for synthesis of wild-type phosphinothricin dehydrogenase engineered strain E. coli BL21(DE3)/pETDuet-LcGDH.

Figure 1:
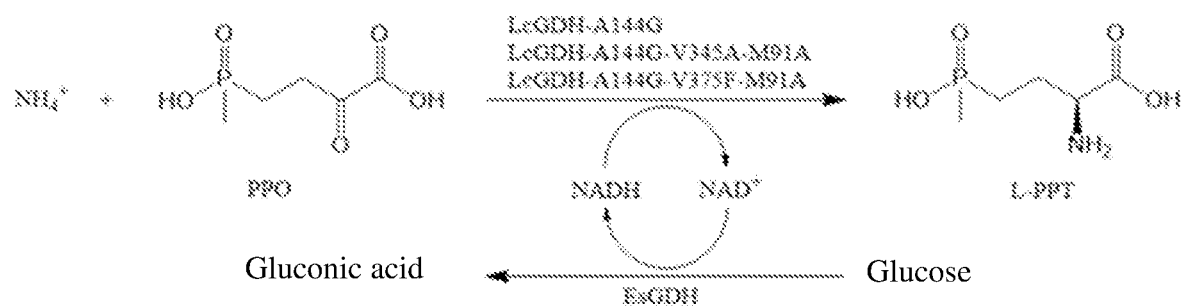
FIG. 1 is a schematic diagram of the reaction for preparing L-phosphinothricin through the asymmetric reductive amination of the intermediate product 2-carbonyl-4-(hydroxymethylphosphono)-butyric acid by the phosphinothricin dehydrogenase mutant coupled with glucose dehydrogenase.

Then, a glucose dehydrogenase gene EsGDH (having a nucleotide sequence with a GenBank accession number of KM817194.1) was obtain by cloning from *Exiguobacterium sibiricum* ZJBML01011, and then constructed onto NdeI of MCS2 (multiple cloning site 2) of the recombinant expression vector pETDuet-LcGDH by One Step Cloning Kit of Vazyme to obtain a co-expression vector pETDuet-LcGDH-EsGDH. The co-expression vector was transferred into E. coli BL21(DE3) to obtain wild-type phosphinothricin dehydrogenase and glucose dehydrogenase starting co-expression strain E. Coli BL21(DE3)/pETDuet-LcGDH-EsGDH. FIG. 1 is a schematic diagram of the reaction for preparing L-phosphinothricin by asymmetric reductive amination of an intermediate product, 2-carbonyl-4-(hydroxymethylphosphono)-butyric acid using the strain.

The preparation of the phosphinothricin dehydrogenase mutant library was achieved by four rounds of site-directed saturation mutation, and the primer design is as shown in Table 1 (wherein in the degenerate bases involved in the primer sequence, N represents A, C, G or T; K represents G or T; and M represents A or C). With the vector pETDuet-LcGDH-EsGDH as a template, a sequence (A144) in Table 1 as a primer, saturation mutation PCR was carried out, which was followed by digestion with DpnI, and transformation of E. coli BL21(DE3). The bacterial cells were then coated to an LB plate containing 50 μg/mL ampicillin, strains were screened by a high-throughput screening method to select dominant strains. Then, the second, third and fourth rounds of site-directed saturation mutation were carried out according to the above steps to screen out dominant strains with higher activity.

TABLE 1

Primer design for phosphinothricin dehydrogenase site-directed saturation mutation

| Mutation | Primer name | Primer sequence (5'-3') |
|---|---|---|
| A144 | A144-Pf | ACCGNNKCCGGATGTTTTTACCAATGC |
|  | A144-Pr | TCCGGMNNCGGTATATCTTTGGTCGGC |
| V345 | V345-Pf | TGGGNNKACAGTTAGCTACTTTGAGTGG |
|  | V345-Pr | AACTGTMNNCCCACCTGCGCTTGCTAA |
| V375 | V375-Pf | AAAATGNNKGATAGCTTTGAAGCAGTATA |
|  | V375-Pr | GCTATCMNNCATTTTTTTGTACAGTTTTTC |
| M91 | M91-Pf | CATGTGGNNKACCCTGAAGTGCGGGATT |
|  | M91-Pr | CAGGGTMNNCCACATGCTCAGTGCTTTAA |

The mutation PCR system (100 μL) consisted of 25 μL of 2-fold Phanta Max buffer, 1 μL of dNTPs, 1 μL of each of upper and lower primers for mutation, 1 μL of template, 0.5 μL of Phanta Super-Fidelity DNA polymerase, and ddH₂O making up to 50 μL. PCR conditions: pre-denaturation at 95° C. for 5 min, 30 cycles: 90° C. for 30 seconds, 62° C. for 30 seconds, 72° C. for 7 min, and final extension at 72° C. for 5 min. The PCR results were subjected to DNA agarose gel electrophoresis for positive verification, the PCR products were subjected to template digestion with DpnI enzyme at 37° C. and 220 rpm for 1 h, and inactivation at 65° C. for 1 min. The PCR products were transferred through heat-shock, E. coli BL21(DE3) was activated, placed at 37° C. and 220 rpm to culture for 1 hour, and then coated on an LB plate containing 50 µg/mL ampicillin resistance to culture upside down at 37° C. overnight. The obtained mutants were screened for dominant mutants according to the method of Example 3, and the obtained dominant strains were sent to Hangzhou Tsingke Biotechnology Co., Ltd. for sequencing and verification, and stored. The following co-expression strains with the mutant phosphinothricin dehydrogenase gene were screened out:
(1) E. coli BL21(DE3)/pETDuet-1-LcGDH(A144G)-EsGDH: The expressed phosphinothricin dehydrogenase (LcGDH) has a mutation A144G.
(2) E. coli B L21(DE3)/pETDuet-1-LcGDH(A144G-V345A-M91A)-EsGDH: The expressed phosphinothricin dehydrogenase (LcGDH) has three amino acid residue mutations, namely A144G, V345A and M91A.
(3) E. coli BL21(DE3)/pETDuet-1-LcGDH(A144G-V375F-M91A)-EsGDH: The expressed phosphinothricin dehydrogenase (LCGDH) has three amino acid residue mutations, namely A144G, V375F and M91A.

Example 3: Induced expression of phosphinothricin dehydrogenase mutant engineered bacteria The wild-type phosphinothricin dehydrogenase and glucose dehydrogenase starting co-expression strain E. coli BL21(DE3)/pETDuet-1-LcGDH-EsGDH, and the following three phosphinothricin dehydrogenase mutant and glucose dehydrogenase co-expression strains:
E.coli BL21(DE3)/pETDuet-1-LcGDH(A144G)-EsGDH, E. coli
BL21(DE3)/pETDuet-1-LcGDH(A144G-V345A-M91A)-EsGDH, and
E. coli BL21(DE3)/pETDuet-1-LcGDH(A144G-V375F-M91A)-EsGDH, from Example 2, were each inoculated into LB liquid medium containing ampicillin with a final concentration of 50 µg/mL, and cultured at 37° C. for 8 hours. The cells were then inoculated at a volume concentration of 2% into fresh LB liquid medium containing ampicillin with a final concentration of 50 µg/mL, and cultured at 37° C. and 180 rpm for 2 hours. Then IPTG with a final concentration of 0.1 mM was added to the culture. The cells were then cultured at 18° C. for 14 hours, and then centrifuged at 4° C. and 8,000 rpm for 10 min to obtain the corresponding wet cells.

Figure 2:
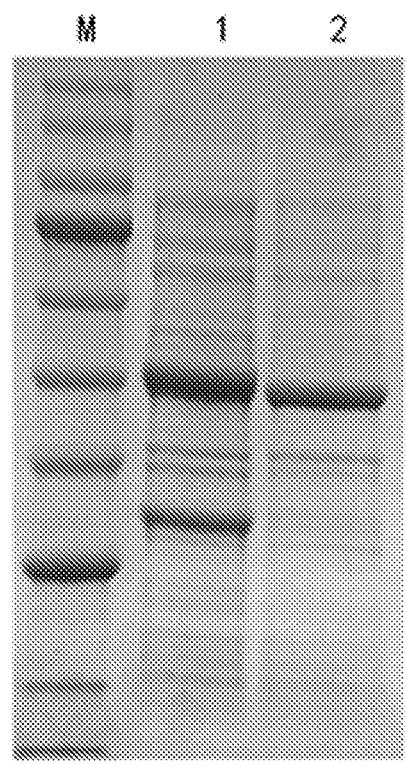
FIG. 2 is an SDS-PAGE diagram for LcGDH and EsGDH coupled enzymatic reaction in Example 3, lane 1: protein ladder; lane 2: recombinant E. coli cells comprising EsGDH; lane 3: recombinant E. coli cells without EsGDH expression.

The cells obtained above produced corresponding proteins, which can be used for preparing protein pure enzyme liquid or preparing L-phosphinothricin by asymmetrically aminating 2-carbonyl-4-(hydroxymethylphosphono)-butyric acid with the crude enzyme liquid. FIG. 2 is an SDS-PAGE diagram for LcGDH and EsGDH coupled enzymatic reaction, lane 1: protein ladder; lane 2: recombinant E. coli cells comprising EsGDH; lane 3: recombinant E. coli cells without EsGDH expression.

Example 4: Mutation library screening

The wild-type phosphinothricin dehydrogenase and glucose dehydrogenase starting co-expression wet cells or the phosphinothricin dehydrogenase mutant and glucose dehydrogenase co-expression wet cells prepared by the method of Example 3 were used as the catalyst, the intermediate product 2-carbonyl-4-(hydroxymethylphosphono)-butyric acid was used as the substrate, and glucose was used as the coenzyme regeneration substrate. To them, ammonium sulfate was added, trace NADH was exogenously added, and a 100 mM phosphate buffer at pH 7.4 was used as the reaction medium, thereby constituting a 1 mL reaction system, wherein the dosage of the catalyst was 20 g/L based on the final concentration of wet cells, the final concentration of the substrate was 100 mM, the final concentration of glucose was 125 mM, and the final concentration of ammonium sulfate was 150 mM. The reaction was allowed to proceed at 35° C. and 600 r/min for 5 min. 50 µL of the reaction mixture was taken, and 5 µL of hydrochloric acid was added thereto to stop the reaction. The reaction mixture was diluted 100 time. 200 µl of the diluted reaction mixture and 400 µL of a derivatization reagent (borate buffer containing 15 mM o-phthalaldehyde and 15 mM N-acetyl-L-cysteine, pH=9.8) were subjected to derivatization at 30° C. for 5 min, then 400 µL of ultra-pure water was added to make up to 1 mL. The mixture was centrifuged at 12,000 rpm for 1 min. The supernatant was passed through a 0.22 µM microfiltration membrane. The filtrate was collected as a liquid phase sample, and detected by HPLC for 2-carbonyl-4-(hydroxymethylphosphono)-butyric acid, L-phosphinothricin, D-phosphinothricin and e.e value. The dominant mutants were screened out using the concentration of product L-phosphinothricin and the enantiomeric excess e.e. as the indexes. The experimental results are shown in Table 2.

Liquid chromatographic conditions for the determination of 2-carbonyl-4-(hydroxymethylphosphono)-butyric acid: chromatographic column, Unitary®C18 (4.6×250mm, Acchrom, China); mobile phase, acetonitrile : 50 mM ammonium dihydrogen phosphate solution (pH 3.8, containing 10% tetrabutyl ammonium hydroxide) in a volume ratio of 12:88; flow rate, 1 mL/min; detection wavelength, 232 nm; injection volume, 10 82 L; column temperature, 30° C.; retention time of 2-carbonyl-4-(hydroxymethylphosphono)-butyric acid, 9.7 min.

Liquid chromatographic conditions for the determination of phosphinothricin: chromatographic column, Unitary®C18 (4.6x250mm, Acchrom, China); mobile phase, methanol : 0.05 M ammonium acetate (pH 5.7) in a volume ratio of 10:90; flow rate, 1.0 mL/min; detection wavelength, $E_x$=340 nm, $E_m$=450 nm; injection volume, 10 µL; column temperature, 35° C.; retention time of L-phosphinothricin and D-phosphinothricin, 10.6 min and 12.6 min respectively.

TABLE 2

Whole-cell catalytic performance and stereoselectivity of wild-type LcGDH and mutants thereof

| Biocatalyst | Product concentration (mM) | e.e (%) |
| --- | --- | --- |
| E. coli BL21 (DE3)/pETDuet-1-LcGDH-EsGDH | 0.889 | 99.5 |
| E. coli BL21 (DE3)/pETDuet-1-LcGDH(A144G)-EsGDH | 20.265 | 99.5 |
| E. coli BL21(DE3)/pETDuet-1-LcGDH(A144G-V345A-M91A)-EsGDH | 28.572 | 99.5 |
| E. coli BL21(DE3)/pETDuet-1-LcGDH(A144G-V375F-M91A)-EsGDH | 31.429 | 99.5 |

Note:
A144G-V375F-M91A represents the mutation at amino acid residue 144 from A to G, at amino acid residue 375 from V to F, and at position 91 from M to A in LcGDH.

Example 4: Purification of wild-type phosphinothricin dehydrogenase and mutants thereof The phosphinothricin dehydrogenase engineered bacterium and the dominant mutants constructed in Example 1 were prepared into corresponding wet bacterial cells according to the method of Example 2. 0.2 g of wet cells of each of the wild-type phosphinothricin dehydrogenase engineered bacterium and the phosphinothricin dehydrogenase mutant engineered bacteria were suspended in 10 ml of a binding buffer (100 mM sodium phosphate buffer containing 0.3 M NaCl, pH 7.4), ultrasonically crushed for 15 min (ice bath, power 400 W, crushing for 1 s followed by pausing for 5 s), and centrifuged at 4° C. and 12,000 r/min for 20 min. The supernatant was taken as the sample. The protein was purified using Ni affinity column (1.6×10 cm, Bio-Rad, USA) as follows: (1) The Ni column was equilibrated with 5 column volumes of a binding buffer (50 mM sodium phosphate buffer containing 0.3 M NaCl, pH 7.4) until the baseline was stable. (2) Samples were loaded at a flow rate of 1 mL/min, and the injection volume was 25-40 mg/mL protein, so that the target protein was adsorbed on the Ni column. (3) Six column volumes of buffer A (50 mM sodium phosphate buffer containing 0.3 M NaCl and 30 mM imidazole, pH 7.4) was used to wash out the miscellaneous proteins at a flow rate of 1 mL/min until the baseline was stable. (4) The target protein was collected by eluting with buffer B (50 mM sodium phosphate buffer containing 0.3 M NaCl and 500 mM imidazole, pH 7.4) at a flow rate of 1 mL/min. The target protein was dialyzed overnight in a 20 mM phosphate buffer at pH 7.4, and the trapped solutions were collected to obtain 10 ml of pure wild-type phosphinothricin dehydrogenase and 10 ml of pure mutant phosphinothricin dehydrogenase, respectively. (5) The Ni column was washed with 5 column volumes of a binding buffer (50 mM sodium phosphate buffer containing 0.3 M NaCl, pH 8.0) until the baseline was stable, and the Ni column was stored in 5 column volumes of ultra-pure water containing 20% ethanol.

Example 5: Detection of specific enzyme activity of wild-type phosphinothricin dehydrogenase and mutants thereof Definition of enzyme activity unit (U): the amount of an enzyme required to produce 1 μmol of L-phosphinothricin per minute at 35° C. and pH 7.4 is defined as one enzyme activity unit, U. Specific enzyme activity is defined as the number of units of activity per milligram of enzyme protein, U/mg.

Standard conditions for enzyme activity detection: 100 mM 2-carbonyl-4-(hydroxymethylphosphono)-butyric acid, 10 mM NADH, 0.02 μg/μL enzyme liquid (prepared by the method of Example 4), reaction at 30° C., pH 7.4, and 600 r/min for 10 min, and HPLC analysis according to the method of Example 3.

The protein concentrations were determined using the BCA protein assay kit (NanJing KeyGen Biotech Co., Ltd., Nanjing), as shown in Table 3.

TABLE 3

Specific enzyme activity of wild-type phosphinothricin dehydrogenase and mutants thereof

| Biocatalyst | Relative enzyme activity (%) | e.e (%) |
|---|---|---|
| LcGDH | 100[a] | 99.5 |
| LcGDH(A144G) | 2279.5 ± 16.5 | 99.5 |
| LcGDH(A144G + V345A + M91A) | 3125.8 ± 5.8 | 99.5 |
| LcGDH(A144G + V375F + M91A) | 3485.2 ± 22.2 | 99.5 |

[a]The initial enzyme activity of each wild-type phosphinothricin dehydrogenase was designated as 100% under standard conditions.

Example 6: Determination of kinetic parameters of wild-type phosphinothricin dehydrogenase and mutants thereof The kinetic parameters of wild-type phosphinothricin dehydrogenase and mutants thereof were investigated, wherein 2-carbonyl-4-(hydroxymethylphosphono)-butyric acid was used as the substrate with a concentration set at 2-10 mM (2, 4, 6, 8, and 10 mM), sufficient coenzyme (10 mM) was added, and 100 μL of pure enzyme liquid (collected by the method of Example 4) was added.

The reaction system was set as 500 μL. The pure enzyme liquid collected in Example 4 was diluted 10 times with a 100 mM phosphate buffer at pH 7.4, 100 μL was taken, and the substrate and the exogenous coenzyme NADPH were added thereto. A 100 mM phosphate buffer at pH 7.4 was used as the reaction medium. The system was allowed to react at 35° C. and 600 rpm for 10 min and then sampled. The reaction mixture was detected by HPLC for determination of the concentration of L-phosphinothricin (the same as in Example 3).

Kcat, $v_{max}$, and $K_m$ can be calculated by double-reciprocal plot. The results are shown in Table 4. By comparing $k_{cat}$ and $K_m$, it can be found that the $K_m$ value of LcGDH for 2-carbonyl-4-(hydroxymethylphosphono)-butyric acid was 8.56 mM, and the affinity of the remaining mutants for 2-carbonyl-4-(hydroxymethylphosphono)-butyric acid tended to increase. The catalytic efficiency $k_{cat}/K_m$ of the mutant LcGDH-(A144G-V375F-M91A)-EsGDH for 2-carbonyl-4-(hydroxymethylphosphono)-butyric acid reached 169.25 mM$^{-1}$, 147.17 times that of the parent ($k_{cat}/K_m$=1.15·mM$^{-1}$).

TABLE 4

Comparison of kinetic parameters between parent LcGDH and mutants thereof

| Enzyme | $k_{cat}$ (s$^{-1}$)[a] | $K_m$ (mM) | $k_{cat}/K_m$ (s$^{-1}$*mM) |
|---|---|---|---|
| LcGDH | 9.88 | 8.56 | 1.15 |
| LcGDH(A144G) | 428.12 | 4.54 | 94.30 |
| LcGDH(A144G + V345A + M91A) | 533.25 | 4.22 | 126.36 |
| LcGDH(A144G + V375F + M91A) | 736.22 | 4.35 | 169.25 |

Figure 3:
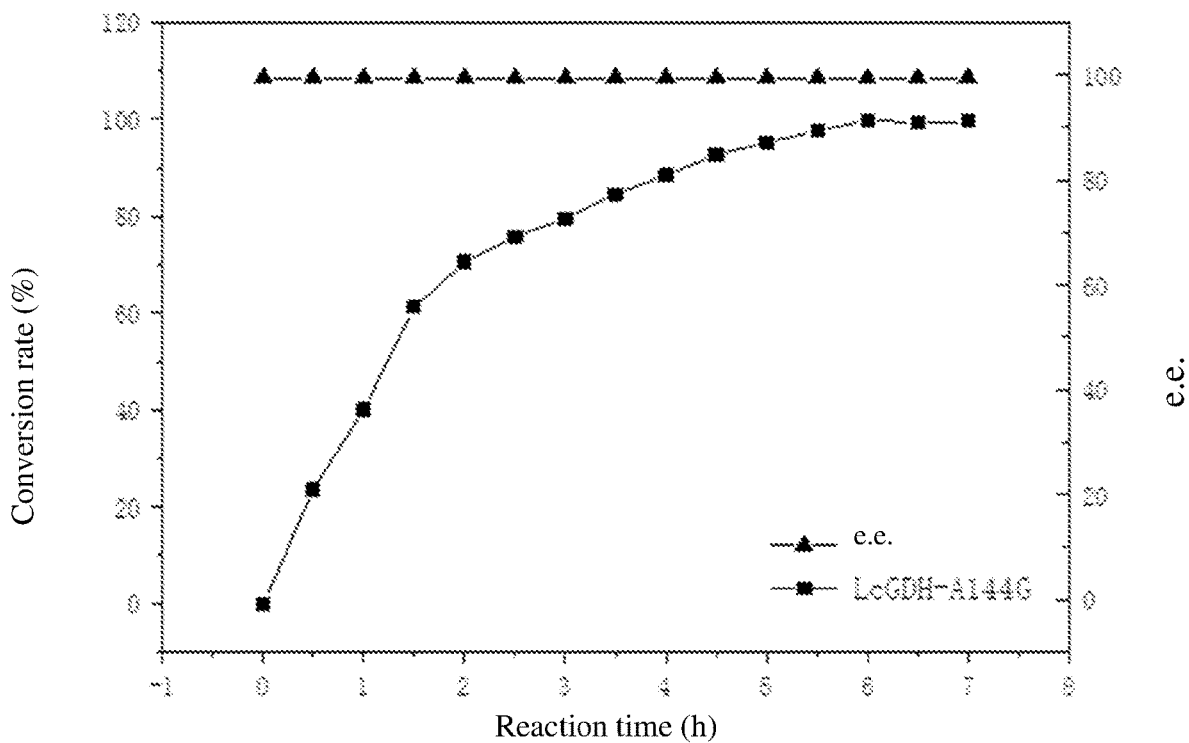
FIG. 3 is a reaction process diagram for the asymmetric reductive amination of 2-carbonyl-4-(hydroxymethylphosphono)-butyric acid using phosphinothricin dehydrogenase mutant LcGDH (A144G) coupled with glucose dehydrogenase. In the reaction system, 1 mM NAD⁺coenzyme was additionally added.

Example 7: Asymmetric reductive amination of 2-carbonyl-4-(hydroxymethylphosphono)-butyric acid using phosphinothricin dehydrogenase mutant LcGDH-A144G coupled with glucose dehydrogenase 1 g of E. coli BL21(DE3)/LcGDH(A144G)-EsGDH wet cell prepared by the method of Example 2 was re-suspended with 40 mL of a phosphate buffer (100 mM) at pH 7.4, 2-carbonyl-4-(hydroxymethylphosphono)butyric acid with a final concentration of 100 mM, glucose with a final concentration of 125 mM, and ammonium sulfate with a final concentration of 125 mM were added to constitute a reaction system of 50 mL to react at 35° C. and a magnetic stirring speed of 600 rpm, and ammonia was fed to maintain the pH of the reaction mixture at 7.4. The production and e.e. change of the product L-phosphinothricin during the reaction were detected by the liquid phase method shown in Example 3. The reaction progress curve is shown in FIG. 3, which shows that the product concentration gradually increased with the passage of time, the reaction was completed within 6 hours, the substrate conversion rate was greater than 99%, and the e.e. value of the product always remained above 99.5%.

Figure 4:
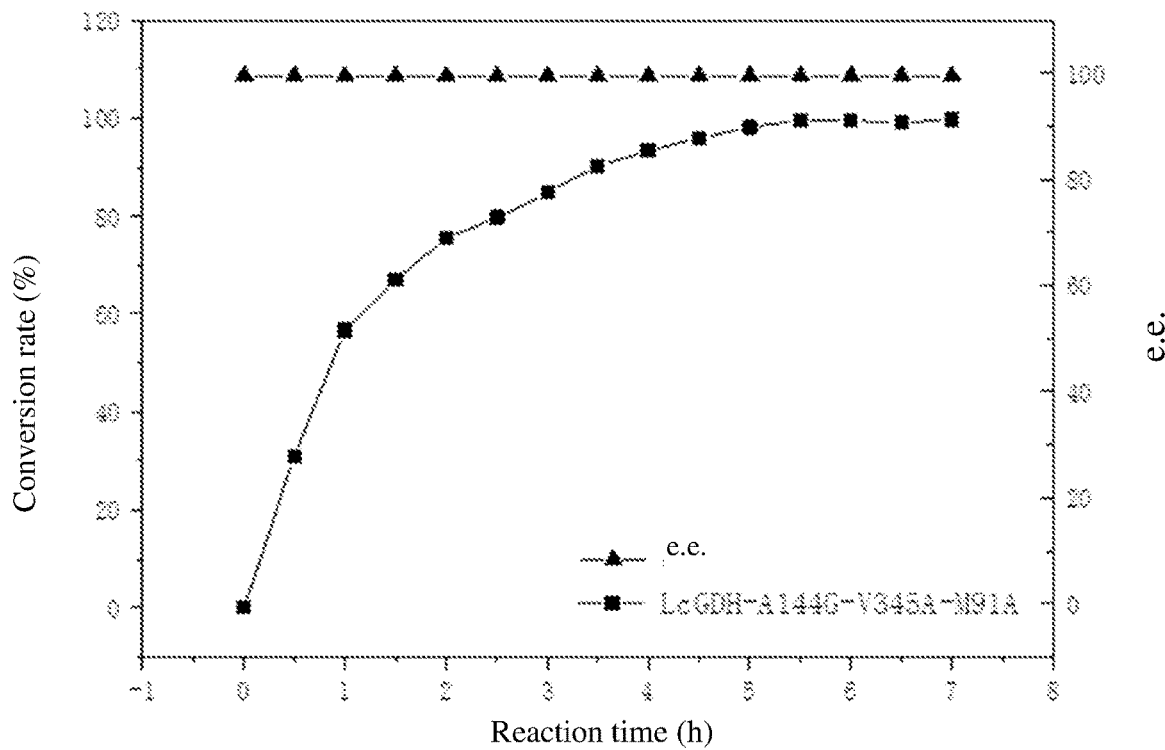
FIG. 4 is a reaction process diagram for the asymmetric reductive amination of 2-carbonyl-4-(hydroxymethylphosphono)-butyric acid using phosphinothricin dehydrogenase mutant LcGDH (A144G-V345A-M91A) coupled with glucose dehydrogenase. In the reaction system, 1 mM NAD⁺coenzyme was additionally added.

Example 8: Asymmetric reductive amination of 2-carbonyl-4-(hydroxymethylphosphono)-butyric acid using phosphinothricin dehydrogenase mutant LcGDH(A144G-V345A-M91A)-EsGDH coupled with glucose 1 g of E. coli BL21(DE3)/LcGDH-(A144G-V345A-M91A)-EsGDH wet cell prepared by the method of Example 2 was re-suspended with 40 mL of a phosphate buffer (100 mM) at pH 7.4, 2-carbonyl-4-(hydroxymethylphosphono)butyric acid with a final concentration of 100 mM, glucose with a final concentration of 125 mM, and ammonium sulfate with a final concentration of 125 mM were added to constitute a reaction system of 50 mL to react at 35° C. and a magnetic stirring speed of 600 rpm, and ammonia was fed to maintain the pH of the reaction mixture at 7.4. The production and e.e. change of the product L-phosphinothricin during the reaction were detected by the liquid phase method shown in Example 3. The reaction progress curve is shown in FIG. 4, which shows that the product concentration gradually increased with the passage of time, the reaction was completed within 5.5 hours, the substrate conversion rate was greater than 99%, and the e.e. value of the product always remained above 99.5%.

Figure 5:
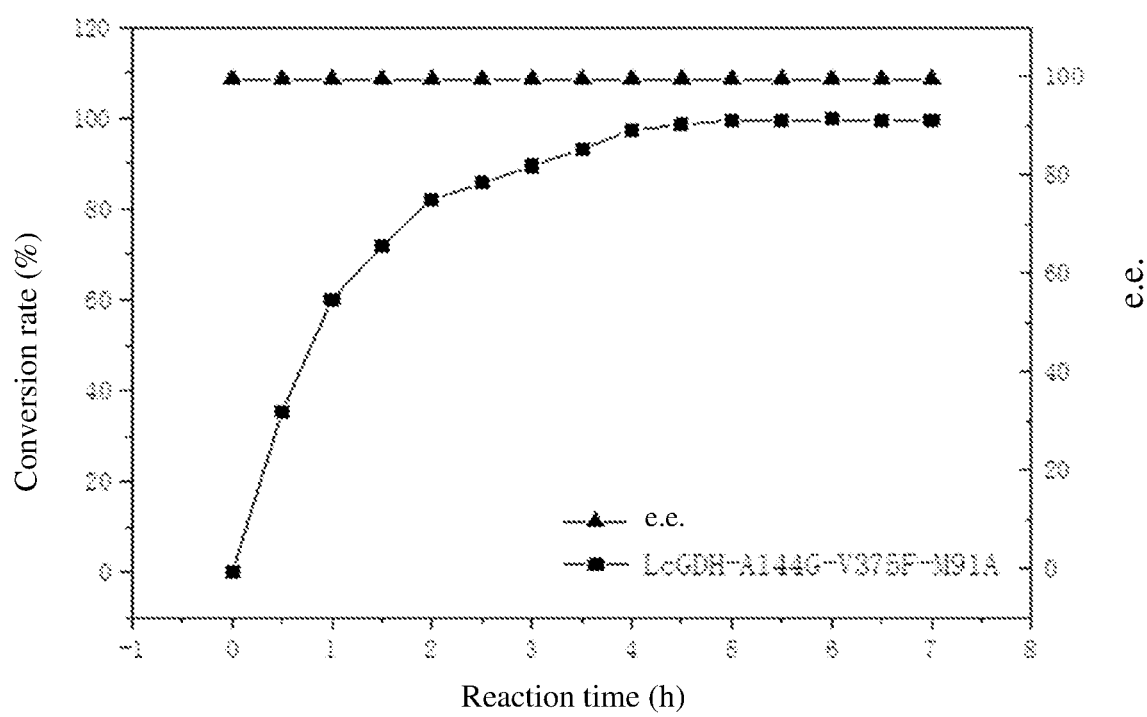
FIG. 5 is a reaction process diagram for the asymmetric reductive amination of 2-carbonyl-4-(hydroxymethylphosphono)-butyric acid using phosphinothricin dehydrogenase mutant LcGDH (A144G-V375F-M91A) coupled with glucose dehydrogenase. In the reaction system, 1 mM NAD⁺coenzyme was additionally added.

Example 9: Asymmetric reductive amination of 2-carbonyl-4-(hydroxymethylphosphono)-butyric acid using phosphinothricin dehydrogenase mutant LcGDH-(A144G-V375F-M91A)-EsGDH coupled with glucose dehydrogenase 1 g of E. coli BL21(DE3)/LcGDH-(A144G-V375F-M91A)-EsGDH wet cell prepared by the method of Example 2 was re-suspended with 40 mL of a phosphate buffer (100 mM) at pH 7.4, 2-carbonyl-4-(hydroxymethylphosphono)butyric acid with a final concentration of 100 mM, glucose with a final concentration of 125 mM, and ammonium sulfate with a final concentration of 125 mM were added to constitute a reaction system of 50 mL to react at 35° C. and a magnetic stirring speed of 600 rpm, and ammonia was fed to maintain the pH of the reaction mixture at 7.4. The production and e.e. change of the product L-phosphinothricin during the reaction were detected by the liquid phase method shown in Example 3. The reaction progress curve is shown in FIG. 5, which shows that the product concentration gradually increased with the passage of time, the reaction was completed within 5 hours, the substrate conversion rate was greater than 99%, and the e.e. value of the product always remained above 99.5%.

The invention claimed is:

1. A method for preparing L-phosphinothricin, characterized in that, 2-carbonyl-4-(hydroxymethylphosphono)-butyric acid as a substrate is allowed to react as catalyzed by a catalyst in the presence of an inorganic amino donor, a coenzyme regeneration and circulation material and a corresponding co-substrate to obtain L-phosphinothricin;

the catalyst is one of the following:
(1) an NADH phosphinothricin dehydrogenase mutant;
(2) a recombinant bacterium capable of expressing the NADH phosphinothricin dehydrogenase mutant or a crude enzyme liquid obtained by lysis of the recombinant bacterium;

wherein the NADH phosphinothricin dehydrogenase mutant is obtained by mutating a wild-type phosphinothricin dehydrogenase obtained from *Lysinibacillus composti*, wherein the NADH phosphinothricin dehydrogenase mutant has the amino acid sequence as set forth in SEQ ID No.2, excepting that the NADH-preferring phosphinothricin dehydrogenase mutant has a mutation site selected from one of the following:
(1) A144G-V375F-M91A;
(2) A144G-V345A-M91A.

2. The method according to claim 1, characterized in that, the coenzyme regeneration and circulation material is selected from glucose dehydrogenase, formate dehydrogenase, or alcohol dehydrogenase.

3. The method according to claim 1, wherein the NADH phosphinothricin dehydrogenase mutant is obtained through a recombinant bacterium that comprises a host cell and a target gene transferred into the host cell, characterized in that, the target gene comprises a gene encoding the NADH phosphinothricin dehydrogenase mutant.

4. The method according to claim 3, wherein the target gene further comprises a gene encoding glucose dehydrogenase.

5. The method according to claim 1, wherein the NADH phosphinothricin dehydrogenase mutant has the mutation site A144G-V375F-M91A.

6. The method according to claim 1, wherein the NADH phosphinothricin dehydrogenase mutant has the mutation site A144G-V345A-M91A.

\* \* \* \* \*